United States Patent [19]
Hunt et al.

[11] Patent Number: 6,066,284
[45] Date of Patent: May 23, 2000

[54] PROCESS FOR THE PRODUCTION OF ENGINEERED PRODUCTS IN WHICH CURING OF THE WOOD IS MONITORED ULTRASONICALLY AND APPARATUS USEFUL THEREFOR

[75] Inventors: Robert N. Hunt, Steubenville, Ohio; Terry L. Thiem, Brights Grove, Canada; Timothy S. McCracken, Aliquippa; Howard S. Duff, Rochester, both of Pa.

[73] Assignee: Bayer Corporation, Pittsburgh, Pa.

[21] Appl. No.: 09/207,341

[22] Filed: Dec. 8, 1998

[51] Int. Cl.$^7$ .......................................................... B27N 3/00
[52] U.S. Cl. ............................ 264/407; 264/83; 264/109; 425/135; 425/174.2
[58] Field of Search ........................... 264/407, 83, 109; 425/135, 174.2

[56] References Cited

U.S. PATENT DOCUMENTS

| | | | |
|---|---|---|---|
| 4,100,328 | 7/1978 | Gallagher | 428/407 |
| 4,393,019 | 7/1983 | Geimer | 264/83 |
| 4,517,147 | 5/1985 | Taylor | 264/83 |
| 4,546,039 | 10/1985 | Horacek et al. | 428/357 |
| 4,609,628 | 9/1986 | Aschenbeck | 436/34 |
| 4,684,489 | 8/1987 | Walter | 264/401 |
| 4,850,849 | 7/1989 | Hsu | 425/407 |
| 4,921,415 | 5/1990 | Thomas, III et al. | 264/407 |
| 5,002,713 | 3/1991 | Palardy et al. | 264/109 |
| 5,009,104 | 4/1991 | Johnson | 73/597 |
| 5,179,143 | 1/1993 | König et al. | 524/35 |

OTHER PUBLICATIONS

James B. Wilson's paper entitled, "Isocyanate Adhesives as Binders for Composition Board" which was presented at the symposium "Wood Adhesives—Research, Applications and Needs" held in Madison, Wisconsin on Sep. 23–25, 1980.

Johnson et al "Acoustic Measurement of the Mechanical Properties of Thin Material Specimens" in Aerospace Report #TR–0091(6935–08)–1, May 15, 1992.

"Acoustic Monitoring of Cold–Setting Adhesive Curing in Wood Laminates: Effect of Clamping Pressure and Detection of Defective Bonds" which appreared in Wood and Fiber Science, 28(1), (month unavailable) 1996, pp. 7–14.

"Acoustic Monitoring of Cold–Setting Adhesive Curing in Wood Laminates" which appeared in Int. J. Adhesion and Adhesives, vol. 16 No. 3 (month unavailable) 1996, pp. 165–172.

"Ultrasonic Cure Monitoring of Advanced Composites", David D. Shepard et al, published in the proceedings of the 42nd International SAMPE Symposium, May 4–8, 1997.

*Primary Examiner*—Mary Lynn Theisen
*Attorney, Agent, or Firm*—Joseph C. Gil; Lyndanne M. Whalen

[57] ABSTRACT

Cure of the binder used to produce a lignocellulosic composite material in a press is monitored by (1) inserting a transmitter probe and a receiver probe into the composite-forming mixture at parallel points; (2) passing an ultrasonic signal from the transmitter probe through the composite-forming mixture to the receiver probe; (3) measuring the pulse velocity of the ultrasonic signal; and (4) comparing the measured pulse velocity to that of a standard (i.e., velocity of pulse through a composite article in which the binder is completely cured). When the measured velocity and the velocity of the standard are equal, the composite article is removed from the press. This technique is particularly useful for monitoring the commercial production of composite and engineered wood products.

7 Claims, 6 Drawing Sheets

PROCESS FOR THE PRODUCTION OF ENGINEERED PRODUCTS IN WHICH CURING OF THE WOOD IS MONITORED ULTRASONICALLY AND APPARATUS USEFUL THEREFOR

BACKGROUND OF THE INVENTION

The present invention relates to a process for monitoring the cure of a binder, particularly an isocyanate-terminated prepolymer binder, during the production of engineered or composite lignocellulosic (e.g., wood) products and to an apparatus useful therefor.

Composite wood products such as oriented strand board, particle board and flake board are generally produced by blending a binder composition with wood flakes, wood strips or strands, pieces of wood or other comminuted lignocellulosic materials. This blended composition is then typically formed into a mat which is compressed between heated platens or plates to set the binder and bond the flakes, strands, strips, pieces, etc. together in densified form. Conventional processes are generally carried out at temperatures of from about 150 to about 205° C. Steam is used when the board thickness prohibits the transfer of heat from the press platens to the center of the board. Steam injection during the press closing cycle enables the center of the board to be preheated before the press is closed and ensures a complete cure throughout the thickness of the board. The conventional processes also generally require that the moisture content of the lignocellulosic material be between 2 and 8% before it is blended with the binder.

Binder compositions which have been used in making such composite wood products include phenol formaldehyde resins, urea formaldehyde resins and isocyanates. See, for example, James B. Wilson's paper entitled, "Isocyanate Adhesives as Binders for Composition Board" which was presented at the symposium "Wood Adhesives-Research, Applications and Needs" held in Madison, Wis. on Sep. 23–25, 1980, in which the advantages and disadvantages of each of these different types of binders are discussed.

Isocyanate binders are commercially desirable because they have high adhesive and cohesive strength, flexibility in formulation, versatility with respect to cure temperature and rate, excellent structural properties, the ability to bond with lignocellulosic materials having high water contents, and no formaldehyde emissions. The disadvantages of isocyanates are difficulty in processing due to their high reactivity, adhesion to platens, lack of cold tack, high cost and the need for special storage.

Isocyanate prepolymers are among the preferred isocyanate materials which have been used in binder compositions to solve various processing problems, particularly adhesion to press platens and high reactivity. U.S. Pat. No. 4,100,328, for example, discloses isocyanate-terminated prepolymers which improve product release from a mold. U.S. Pat. No. 4,609,513 also discloses a process in which an isocyanate-terminated prepolymer binder is used to improve product release. A binder composition in which a particular type of isocyanate prepolymer is used to improve adhesiveness at room temperature is disclosed in U.S. Pat. No. 5,179,143.

A major processing difficulty encountered with isocyanate binders is the rapid reaction of the isocyanate with water present in the lignocellulosic material and any water present in the binder composition itself. One method for minimizing this difficulty is to use only lignocellulosic materials having a low moisture content (i.e., a moisture content of from about 3 to about 8%). This low moisture content is generally achieved by drying the cellulosic raw material to reduce the moisture content. Such drying is, however, expensive and has a significant effect upon the economics of the process. Use of materials having low moisture contents is also disadvantageous because panels made from the dried composite material tend to absorb moisture and swell when used in humid environments.

Another approach to resolving the moisture and isocyanate reactivity problem is disclosed in U.S. Pat. No. 4,546,039. In this disclosed process, lignocellulose-containing raw materials having a moisture content of up to 20% are coated with a prepolymer based on a diphenylmethane diisocyanate mixture. This prepolymer has a free isocyanate group content of about 15 to about 33.6% by weight and a viscosity of from 120 to 1000 mPa·s at 25° C. This prepolymer is prepared by reacting (1) about 0.05 to about 0.5 hydroxyl equivalents of a polyol having a functionality of from 2 to 8 and a molecular weight of from about 62 to about 2000 with (2) one equivalent of a polyisocyanate mixture containing (a) from 0 to about 50% by weight of polyphenyl polymethylene polyisocyanate and (b) about 50 to about 100% by weight isomer mixture of diphenylmethane diisocyanate containing 10–75% by weight of 2,4'-isomer and 25–90% by weight of 4,4'-isomer.

U.S. Pat. No. 5,002,713 discloses a method for compression molding articles from lignocellulosic materials having moisture contents of at least 15%, generally from 15 to 40%. In this disclosed method, a catalyst is applied to the lignocellulosic material. A water-resistant binder is then applied to the lignocellulose with catalyst and the coated materials are then compression shaped at a temperature of less than 400° F. to form the desired composite article. The catalyst is a tertiary amine, an organometallic catalyst or a mixture thereof. The binder may be a hydrophobic isocyanate such as any of the polymeric diphenylmethane diisocyanates, m- and p-phenylene diisocyanates, chlorophenylene diisocyanates, toluene diisocyanates, toluene triisocyanates, triphenylmethane triisocyanates, diphenylether-2,4,4'-triisocyanate and polyphenol polyisocyanates. The catalyst is included to ensure that the isocyanate/water reaction is not slowed to such an extent that the pressing time necessary to produce the molded product is significantly increased.

Pressing of wafer board, oriented strand board, and parallel strand lumber using steam injection and a conventional binder such as a urea-formaldehyde resin or a polymeric diphenylmethane diisocyanate (MDI) is known. Examples of such known pressing processes are disclosed in U.S. Pat. Nos. 4,684,489; 4,393,019; 4,850,849; and 4,517,147.

The processes disclosed in U.S. Pat. Nos. 4,517,147 and 4,684,489 require pressing and steaming of wood mat in several stages. First, the air present in the mat is driven out. The wood strands are then softened to allow compression to a higher density and the center of the mat is preheated to a uniform temperature. It is apparent from these disclosures that resin cure must be monitored and the press closing and steaming cycles must be controlled to minimize the amount of resin prematurely cured before the press is fully closed and to optimize board properties.

The completeness of binder cure may, of course, be determined by destructive testing of samples which have been permitted to cure for varying amounts of time under the process conditions. The cure time to be used during the production process is determined on the basis of the sample which had completely cured in the least amount of time. The disadvantages of this method are readily apparent. Valuable product is destroyed in the testing. Further, any variation in wood composition, extent of binder dispersion on the wood particles, etc. or processing conditions which would affect the rate of binder cure are not taken into consideration in the above-described method.

Those in the art have therefore continued to seek a reliable, non-destructive method for monitoring the cure of the binder in composite materials during the production process.

One approach which is considered to be promising is the use of ultrasonic waves to determine the viscosity or some other dynamic property of the binder. Johnson et al discuss the theory behind use of ultrasonic waves in such applications in their proposal entitled "Acoustic Measurement of the Mechanical Properties of Thin Material Specimens" in Aerospace Report # TR-0091(6935-08)-1.

In U.S. Pat. No. 5,009,104, the viscosity of a composite part as it is cured is measured. In this disclosed method, the composite material is secured in a vacuum bag and carried by a tool having an aperture which accommodates an acoustic wave guide coupled directly to the part. Pulses of ultrasound energy are directed through the wave-guide and the amplitude of the reflected pulses is monitored. It is not possible by this method to determine viscosity change at any point of the composite article which is not within the aperture of the tool. This method is effective when a homogeneous, semi-liquid resin that will conform to the shape of the tool and allow efficient coupling of the acoustic wave between the tool and composite resin is used. However, in the production of engineered lumber, particularly oriented strand board, the wood mat is not homogeneous. This lack of homogeneity causes a multitude of scattered acoustic waves that when recombined at the receiving transducer generate a complex signal that changes shape and amplitude. Scattered waves should be eliminated because they interfere with the measurement of reflected pulse amplitude. The method disclosed in U.S. Pat. No. 5,009,104 will not therefore be effective for monitoring non-homogeneous media.

In their article entitled "Acoustic Monitoring of Cold-Setting Adhesive Curing in Wood Laminates: Effect on Clamping Pressure and Detection of Defective Bonds" which appeared in *Wood and Fiber Science,* 28(1), 1996, pp. 7–14, Biernacki et al report the results of their study of an ultrasonic method for monitoring the bonding process and assessing the quality of cured bonds in wood laminates. Monitoring was conducted at normal and at angular (5°) incidence to the bond plane. It was found that defective bonds could be detected using patterns of relative attenuation changes during curing. Selection of optimum clamping pressure could be made based upon the observation that transmission of the ultrasonic waves through uncured bond lines was strongly affected by pressure.

In their article entitled "Acoustic Monitoring of Cold-Setting Adhesive Curing in Wood Laminates" which appeared in *Int. J. Adhesion and Adhesives,* Vol.16, No.3 (1996), pp.165–172, Biernacki et al report that acoustic transmission is sensitive to different bond types and curing phases. It is also reported that a reasonable correlation between the relative coefficient of transmission and the development of strength over time was found. The conclusions stated in this article are, however, based upon the results of tests conducted under very strictly controlled conditions.

The tightly controlled conditions described in the Biernacki et al articles could not, however, be maintained during commercial production of composite wood materials. The Biernacki et al methods are based on a single bond interface. In commercial composite wood production processes, there are a large number of bond interfaces. The scattering of acoustic waves in a non-homogeneous medium such as wood mats would render the Biernacki et al methods ineffective.

In "Ultrasonic Cure Monitoring of Advanced Composites", David D. Shepard et al, published in the proceedings of the 42nd International SAMPE Symposium, May 4–8, 1997, Shepard et al describe a method and apparatus for monitoring the cure of thermosetting resins and composites in which the speed of ultrasonic acoustic waves through the resin or composite is measured. Shepard et al reports that there is a good correlation between the ultrasonic method disclosed therein and the widely used dielectric cure monitoring method. The Shepard et al method requires ultrasonic transducers mounted in the walls of the press. This method may be impractical for existing production presses in which the press would have to be disassembled to mount the transducers. In addition, when the steam press cycle is used, the acoustic noise generated by the high-pressure steam passing through the press platens will generally override the ultrasonic signal from the transducer.

SUMMARY OF THE INVENTION

It is an object of the present invention to provide a process for monitoring the cure of a binder for lignocellulosic materials.

It is also an object of the present invention to provide a nondestructive method for monitoring the cure of an isocyanate-based binder for lignocellulosic materials during the production process.

It is another object of the present invention to provide an apparatus useful for monitoring the cure of the binder used to produce wood composites during the production process.

It is another object of the present invention to provide a process for producing wood composites in a steam injection press in which the steam/press cycle can be optimized by monitoring the amount of cure in the early stages of the cycle.

It is a further object of the present invention to provide a process for producing wood composites with shorter press times than present commercial processes due to the ability to more accurately determine the point in time when the composite binder is completely cured.

These and other objects which will be apparent to those skilled in the art are accomplished by inserting a transmitter probe and a receiver probe into a binder/cellulosic material mixture at parallel points between the top and bottom plates of a press. The transmitter and receiver probes should be positioned sufficiently far apart to allow measurement of the ultrasonic acoustic wave velocity through the binder/cellulose material mixture. An ultrasonic signal is then sent from the transmitter probe through the composite-forming mixture to the receiver probe. The pulse velocity of each wave of the ultrasonic signal as the wave passes through the composite material is then measured. The measured velocity is compared to the velocity of comparable waves passed through a composite article in which the binder is completely cured (i.e., the velocity standard). When the measured velocity and the velocity standard are equal, the composite article is removed from the press.

DETAILED DESCRIPTION OF THE PRESENT INVENTION

Figure 1:
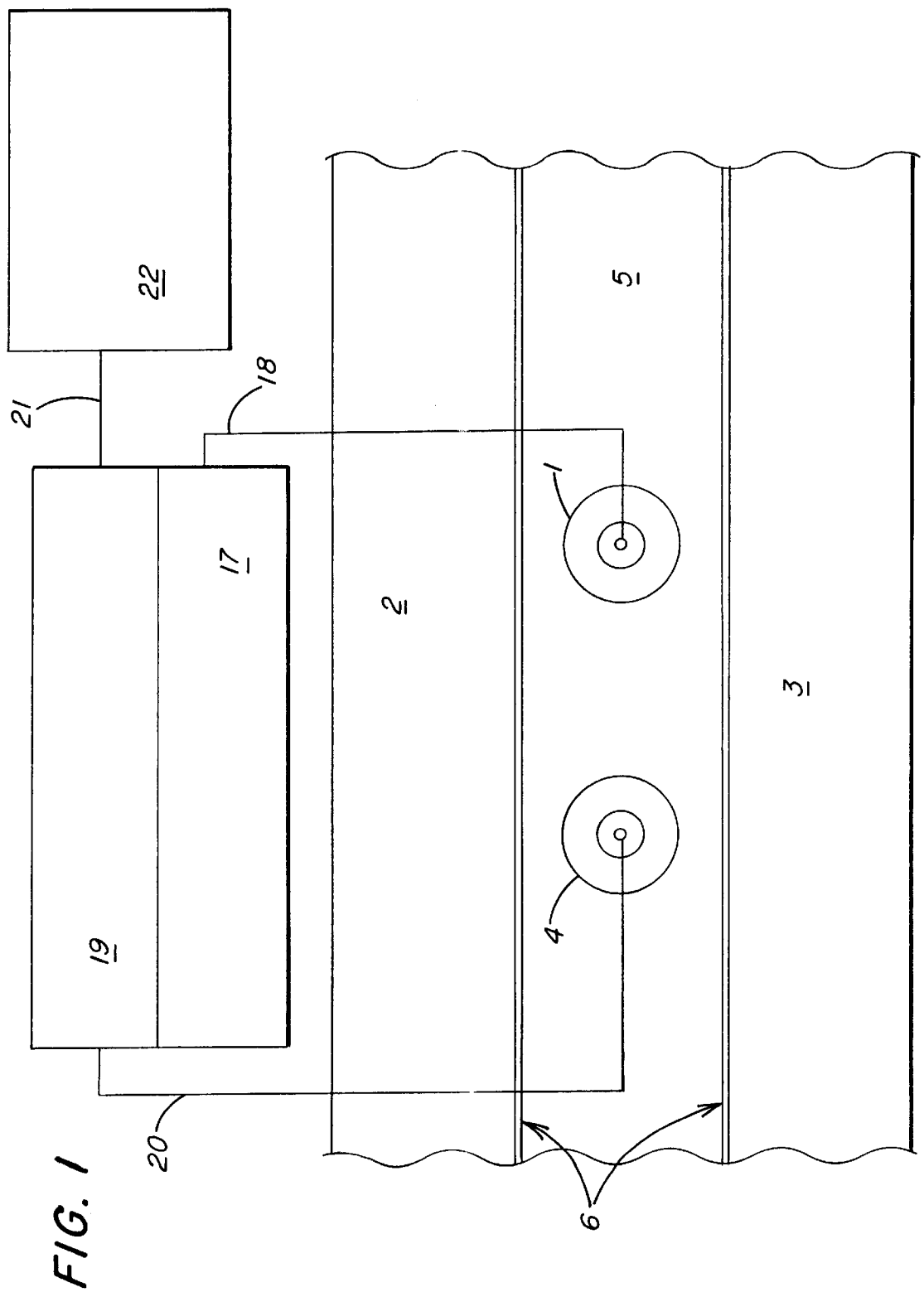
FIG. 1 is a schematic illustration of a side view of an apparatus suitable for monitoring the cure of a binder in accordance with the present invention.

The present invention relates to a process for monitoring the cure of a binder during the production of an engineered lignocellulosic product (e.g., a wood composite material) and to an apparatus useful for such monitoring process.

The process of the present invention will be described in greater detail with reference to the apparatus illustrated in FIGS. 1 and 2.

In the present invention, transmitter probe assembly 1 is inserted into the material 5 from which the composite wood article is to be made (i.e., lignocellulosic material to which binder has been applied such as a wood mat).

The transmitter probe assembly 1 ("transmitter probe") and receiver probe assembly 4 ("receiver probe") are generally identical in structure so that they are interchangeable. As shown in FIG. 2, the transmitter probe 1 and receiver probe 4 are composed of a low frequency (e.g., 60 KHz) ultrasonic transducer 10 which is attached to metal disc 11. Metal disc 11 is adapted to receive small diameter metal rod 12 that acts as a wave-guide. In operation, ultrasonic acoustic waves generated by transducer 10 in transmitter probe 1 are directed by wave guide 12 of transmitter probe 1 into the material 5 being used to produce the composite. The ultrasonic acoustic waves 16 shown in FIG. 2 travel through the composite-forming material 5 to receiver probe 4. Wave guide 12 of receiver probe 4 channels the ultrasonic waves 16 received by receiver probe 4 to transducer 10 of receiver probe 4.

Figure 2:
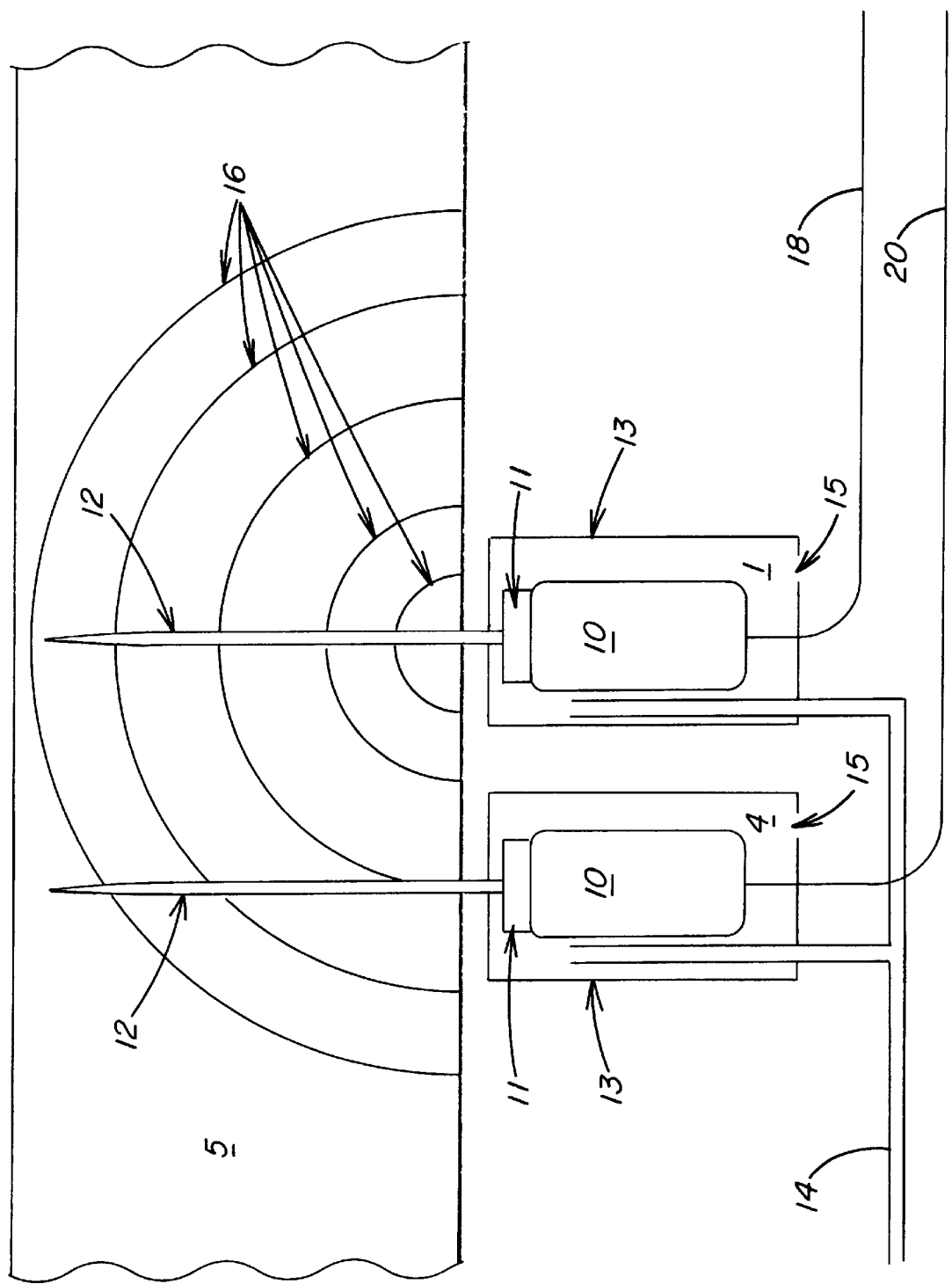
FIG. 2 is schematic illustration of the top view of an ultrasonic probe assembly of the present invention.

To protect transducers 10 from damage due to any steam present during a press cycle, an enclosure such as the lightweight plastic enclosure 13 shown in FIG. 2 may be used to completely encase the transducer 10. If an enclosure 13 is used, that enclosure should be purged with a gas such as, dry air. The dry air may be supplied by supply hose 14 shown in FIG. 2. The gas used to purge enclosure 13 is removed via exit port 15 (FIG. 2) prior to initiating the press cycle.

The composite-forming material 5 is placed between top platen 2 and bottom platen 3 of the press (FIG. 1). The press is usually heated and may have the capability of injecting steam into the composite-forming material 5. Fabric 6 separates composite-forming material 5 and platens 2 and 3. One material which has been found to be particularly useful as fabric 6 is a spunbonded polypropylene fabric that acts as a mold release to prevent wood from bonding to the platens. Fabric 6 may be used to replace the woven stainless steel screen used in conventional presses. Use of fabric 6 rather than steel screens eliminates interference with the ultrasonic signal being transmitted through composite-forming material 5 that would be caused by the stainless steel screen.

Transmitter probe 1 is generally positioned in composite-forming material 5 at a point which is approximately midway between top platen 2 and bottom platen 3 of the steam press. Transmitter probe 1 must be inserted into the composite-forming material 5 in a manner such that at least 10 cm, preferably from about 10 to about 20 cm of the probe are within composite-forming material 5.

Receiver probe 4 is also inserted into composite-forming material 5. Receiver probe 4 is inserted in the composite-forming material 5 next to and on a parallel axis with transmitter probe 1. Receiver probe 4 is also preferably positioned at a point which is approximately midway between top platen 2 and bottom platen 3 of the press. Receiver probe 4 must be inserted into composite-forming material 5 in a manner such that at least 10 cm, preferably from 10 to 20 cm of the probe are within composite-forming material 5.

Once the transmitter probe 1 and receiver probe 4 have been placed in the proper position, transmitter probe 1 is then excited via connecting cable 18 by ultrasonic transducer driver 17 capable of generating a high voltage pulse of from 1 to 12 cycles in duration at a frequency of from about 30 to about 70 KHz. Ultrasonic wave 16 is emitted by transmitter probe 1, through composite-forming material 5, to receiver probe 4. The signal received by receiver probe 4 is conveyed to the signal amplifier 19 via connecting cable 20, where it is amplified and conditioned until a signal level of from about 1 to 10 volts peak to peak is obtained. The amplified signal is then relayed via connecting cable 21 to an analog to digital converter and signal processing computer 22. The digitized signal is processed to reduce noise by time averaging 100 pulses.

The distance between transmitter probe 1 and receiver probe 4 is held constant. The relative change in ultrasonic acoustic wave velocity which corresponds to the degree of binder cure in the wood composite forming material during the press cycle is determined by measuring the time delay between the first half cycle of the transmitted pulse and the first half cycle of the received pulse. Due to the non-homogeneous nature of the lignocellulose material, the initial time delay or velocity of the acoustic wave through the composite-forming material will vary depending on the density and orientation of the lignocellulose strands. When comparing data from multiple runs, it is necessary to shift the velocity trends by adding a velocity offset to each data set so that all runs will have the same starting velocity. The extent of binder cure is indicated by the amount of change in ultrasonic wave velocity from the initial velocity. The cure is monitored by comparing the rate change in velocity of the composite-forming material being processed with a velocity trend graph of a previously established standard press run. A velocity trend graph generated during a press run in which no binder was present is used as a base line so that changes due to temperature and pressure fluctuations during steam injection can be removed. As the binder cure reaches completion, the velocity of the ultrasonic waves will reach a maximum. The press cycle may be terminated when the ultrasonic wave velocity change from the initial velocity equals or exceeds a predetermined "standard" value. The composite article may then be removed from the press.

It is preferred that the outer surface of transmitter probe 1 and receiver probe 4 be treated with a mold release agent so that those probes may be easily removed from the pressed article. Any of the known mold release agents would be suitable. Murphy's soap is an example of a mold release agent which has been found to be particularly useful in the practice of the present invention.

The ultrasonic waves and/or wave velocities may be displayed on a computer monitor (not shown).

Composite articles having a thickness of 2 inches or more are typically produced in a steam press which includes two steam press platens, a steam generator, means for feeding the steam to the steam press platens, a control mechanism for positioning of the platens, a steam regulating mechanism and means for regulating temperature and pressure. Such presses, steam generators, means for feeding steam to the press platens, control means and regulator means are commercially available. Any of the commercially available press equipment may be used in the practice of the present invention. An example of a suitable press is that which is available under the name Newman Hydra Press Model HP-138 from New Machine Company, Greensboro, N.C.

The ultrasonic transducer 10 used in transmitter probe 1 and in receiver probe 4 in the practice of the present invention may be any one of the commercially available transducers which is capable of emitting an ultrasonic signal at from about 30 to about 70 KHz, preferably from about 40 about 60 KHz. An example of a suitable transducer is the N111-0.06-N3.1 60 KHz low frequency, narrow band ultrasonic transducer that is available from NDT International, Inc., West Chester, Pa.

Metal disc 11 used in the apparatus of the present invention (shown in FIG. 2) may be made of any metal but stainless steel, preferably 316 stainless steel, is preferred. The dimensions of metal disc 11 will generally be elected so that disc 11 will match the interface surface of transducer 10 and will be capable of serving as a mount for wave guide rod 12.

Metal disc 11 is generally attached to transducer 10 with an adhesive such as an epoxy, preferably an epoxy of the type which is commercially available under the name Devcon Model 10270 from W.W. Grainger Inc.

The metal rod used as wave-guide 12 in both the transmitter probe 1 and receiver probe 4 may be made of any metal, preferably stainless steel, most preferably a 316 stainless steel. The metal rod should be long enough to extend into composite-forming material 5 far enough to couple the ultrasonic acoustic waves into the composite-forming material 5. The metal rod will generally be from about 10 to about 30 cm. long, preferably about 20 cm. long. The rod will generally have a diameter of from about 6.35 to about 12.7 mm, preferably about 6.35 mm. It is preferred that the diameter of the rod be as small as possible because smaller probes are easier to remove from the composite article and deform the mat less than larger probes.

Probe enclosure 13, if present, is generally made of a material capable of withstanding the composite production process conditions, preferably a plastic such as polyethylene. To minimize the size of the probe, the dimensions of enclosure 13 are generally those minimally necessary to enclose transducer 10 and disc 11.

Ultrasonic transducer driver 17 and signal amplifier 19 are generally packaged as a single unit. Any ultrasonic transducer driver capable of generating a high voltage drive pulse of from 1 to 12 cycles in duration at a frequency of from about 30 to about 70 KHz may be used in the practice of the present invention. Any ultrasonic receiver amplifier capable of conditioning the low level received signal to a level of from about 1 to about 10 volts may be used as amplifier 19. An example of a transducer driver and signal amplifier unit which has been found to be particularly useful in the practice of the present invention is model NDT-910 Ultrasonic Tester available from NDT International, Inc., West Chester, Pa.

Any analog to digital converter board having a minimum of 8 bits of resolution and a bandwidth of greater than 5 MHz may be used to digitize the ultrasonic signals received by receiver probe 4. An example of a converter board which has been successfully used in the practice of the present invention is the Model CS255 which is commercially available from GAGE Applied Sciences, Inc., Quebec, Canada. Any fabric capable of withstanding 100 psi steam that does not melt or stick to the binder present in the composite-forming material, the lignocellulose material, or the platens of the press can be used as fabric 6. An example of a preferred fabric material is Typar spunbound polypropylene landscape fabric manufactured by Reemay, Inc., Old Hickory, Tenn.

The process of the present invention is based upon the recognition that the change in modulus of elasticity (or Young's modulus) resulting from steam pressing of the lignocellulose/binder mixture causes the velocity of ultrasonic waves passing through that mixture to increase. Consequently, as the binder continues to cure under the pressing conditions, the velocity of the ultrasonic waves passing through the composite mixture will increase until the binder has completely cured.

Any of the commercially available binders may be used to produce composite articles in accordance with the present invention. Examples of such commercially available binders include: urea-formaldehyde resins, phenol-formaldehyde resins, and isocyanate-based binder compositions. The most preferred binders are based on polymeric MDI (i.e., polyphenylene polymethylene polyisocyanate), and have a viscosity of less than 500 cps at 25° C. Isocyanate-terminated prepolymers having a viscosity of less than 1500 cps (preferably less than 1000 cps) at 25° C. are also suitable. These isocyanate-terminated prepolymers may be formed by reacting a polyisocyanate mixture and an isocyanate-reactive compound having from about 1 to about 8 hydroxyl groups and a molecular weight of from about 62 to about 6,000 in amounts such that the ratio of equivalents of hydroxyl groups to isocyanate groups is from about 0.001:1 to about 0.20:1, preferably from about 0.004:1 to about 0.1:1. The polyisocyanate mixture is preferably a mixture of polyphenylene polymethylene polyisocyanate (polymeric MDI) and a mixture of diphenylmethane diisocyanate isomers.

In a particularly preferred polyisocyanate prepolymer binder, the polyphenylene polymethylene polyisocyanate is present in the polyisocyanate mixture in an amount of from 50 to about 60% by weight (based on the total weight of the polyisocyanate mixture), preferably from about 50 to about 58% by weight, most preferably from about 52 to about 56% by weight. The mixture of diphenylmethane diisocyanate isomers is present in an amount of from about 40 to 50% by weight (based on the total amount of polyisocyanate mixture), preferably from about 42 to about 50%. The isomer mixture of diphenylmethane diisocyanate may be composed of (a) from about 4 to about 30% by weight (based on the total weight of the isomeric diphenylmethane diisocyanate mixture), preferably from about 5 to about 28% by weight of 2,4'-diphenylmethane diisocyanate and (b) from about 70 to about 96% by weight (based on the total amount of the diphenylmethane diisocyanate isomer mixture), preferably from about 72 to about 95% by weight of 4,4'-diphenylmethane diisocyanate.

The polyisocyanate mixture may be produced in accordance with any of the techniques known in the art. The isomer content of the diphenylmethane diisocyanate may be brought within the desired range, if necessary, by techniques which are well known in the art. One technique for changing isomer content is to add monomeric MDI to a mixture of MDI containing an amount of polymeric MDI which is higher than desired.

Polymeric isocyanates prepared from residues of the toluene diisocyanate production process may optionally be included in the binder composition of the present invention.

The isocyanate-reactive compound used to produce the polyisocyanate prepolymer binder will generally have at least one hydroxyl group, preferably from about 2 to about 8 hydroxyl groups, and most preferably from about 2 to about 4 hydroxyl groups and a molecular weight of from about 62 to about 6000, preferably from about 500 to about 5,000, most preferably from about 1,000 to about 4000. Any of the known isocyanate-reactive materials having at least 1 hydroxyl group satisfying these criteria may be used. Suitable isocyanate-reactive materials include but are not limited to any of the known polyesters and polyethers.

Polyesters which may be used to produce the prepolymer binder include the reaction products of polyhydric (preferably dihydric) alcohols with polybasic (preferably dibasic) carboxylic acids, polycarboxylic acid anhydrides or polycarboxylic acid esters of lower alcohols. The polycarboxylic acid may be aliphatic, cycloaliphatic, aromatic and/or heterocyclic and may optionally be substituted (e.g., by halogen atoms) and/or unsaturated. Specific examples of suitable carboxylic acids and their derivatives are succinic acid, glutaric acid, adipic acid, suberic acid, azelaic acid, sebacic acid, phthalic acid, isophthalic acid, terephthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid anhydride, dimerized and trimerized unsaturated fatty acids (optionally in admixture with monomeric unsaturated fatty acids such as oleic acid), terephthalic acid dimethyl ester and terephthalic acid-bis-glycol ester. Specific examples of suitable alcohols are 1,2-propylene glycol, 1,3-propylene glycol, 1,4-butylene glycol, 2,3-butylene glycol, 1,6-hexanediol, 1,8-octanediol, neopentyl glycol, 1,4-bis-hydroxy-methyl cyclohexane, 2-methyl 1,3-propanediol, glycerol, trimethylol propane, 1,2,6-hexanetriol, 1,2,4-butanetriol, trimethylol ethane, pentaerythritol, quinitol, mannitol, 1,4-cyclohexanedimethylol, sorbitol, formitol, methyl glycoside, diethylene glycol, triethylene glycol, tetraethylene glycol, higher polyethylene glycols, dipropylene glycol, higher polypropylene glycols, dibutylene glycol and higher polybutylene glycols. The polyester may contain terminal carboxyl groups or a small portion of monofunctional ester capped functionalities. Polyesters of lactones (e.g., ε-caprolactone) or of dihydroxy carboxylic acids (e.g., ω-hydroxy caproic acid) may also be used.

Preferred polyesters are prepared from mixtures of phthalic, isophthalic and terephthalic acids with ethylene glycol, diethylene glycol and higher polyethylene glycols.

Polyethers which may be used to produce the prepolymer binder may be produced, for example, by polymerizing epoxides themselves in the presence of a Lewis acid catalyst or by the addition of an epoxide to starter components containing reactive hydrogen atoms such as water, alcohols, ammonia or amines. Epoxides which may be used include ethylene oxide, propylene oxide, butylene oxide, tetrahydrofuran, styrene oxide and epichlorohydrin. Ethylene oxide, propylene oxide and combinations thereof are particularly preferred.

Specific examples of suitable starter components include: ethylene glycol, 1,3-propylene glycol, 1,2-propylene glycol, trimethylol propane, glycerol, sorbitol, 4,4'-dihydroxy diphenyl propane, aniline, ethanolamine, substituted ethanolamines such as methyl ethanolamine and methyl diethanolamine, ethylene diamine, and sucrose. The starter component may be used alone or in admixture with other starter components.

Preferred polyethers are polypropylene oxide adducts started on an amine such as ammonia, ethylene diamine, and substituted ethanolamines.

The polyisocyanate mixture and isocyanate-reactive material used to produce the prepolymer binder are each generally used in quantities such that the ratio of equivalents of hydroxyl groups to isocyanate groups is from about 0.001:1 to about 0.20:1, preferably from about 0.004 to about 0.1:1, most preferably from about 0.005 to about 0.02.

The prepolymer binder may be prepared by reacting the polyisocyanate mixture and hydroxyl compound at temperatures of from about 10 to about 250° C., preferably from about 60 to about 120° C. for a period of from about 1 to about 1500 minutes, preferably from about 30 to about 200 minutes.

Other materials which may optionally be used in the production of the prepolymer binder include polycarbonates, ester carbonates and ether carbonates containing isocyanate-reactive hydrogen atoms.

Lignocellulosic materials which may be bonded in accordance with the present invention include: wood, woodbark, cork, bagasse straw, flax, bamboo, esparto, rice husks, sisal fibers, coconut fibers, wood chips, wood fibers, wood shavings, wood dust, wood flour, kenaf, nut shells, and hulls from cereal grains such as rice and oats. Wood, straw and bagasse are particularly preferred. These materials may be used in the form of granulates, shavings or chips, fibers, strands, spheres or powder. These materials may have a moisture content of from about 2 to about 50%, preferably from about 2 to about 20%.

The binder is added to the lignocellulosic material to be bonded in a quantity of from about 1 to about 20% by weight, based on the total weight of binder plus lignocellulosic material, preferably from about 2 to about 10% by weight. The resultant mixture may then be compressed to form boards or three dimensional, shaped, molded articles under heat and pressure. Suitable temperatures for the compression process are generally in the range of from about 70 to about 250° C., preferably from about 130 to about 205° C. Pressures typically used in compression processes range from about 1 to about 150 bar. Compression times will, of course, be dependent upon the thickness of the product being produced. The compression times required for products made by the process of the present invention are shorter than those required in conventional, commercial compression processes because there is no need to make allowances for variance in bond cure. In addition to time savings, the amount of rejected material and material to be repressed will be substantially reduced.

Multilayered boards or molded parts may be produced in an analogous manner from veneers, paper or woven fabrics by treating the layers with the binder as described above and subsequently pressing them, generally at elevated temperature and pressure. Temperatures of from about 100 to about 250° C. are generally preferred in such processes, with temperatures of from about 130 to about 200° C. being most preferred. The initial compression pressure is preferably in the range of from about 5 to about 150 bar, although the pressure drops towards 0 bar during the compression process in most cases.

The composite products produced in accordance with the present invention are characterized by good appearance, good internal bond properties, good dimensional stability, and excellent exterior durability.

Having thus described our invention, the following examples are given as being illustrative thereof. All parts and percentages given in these examples are parts by weight and percentages by weight, unless otherwise indicated.

EXAMPLES

The following materials were used in the following examples:

Binder Composition: Polymeric MDI having an equivalent weight of 131, an average functionality of 2.8, containing 40% by weight monomeric 4,4'-MDI, 3% by weight monomeric 2,4'-MDI and 2,2'-MDI, and 57% by weight higher molecular weight homologs of MDI.

Lignocellulose Material: mixed hardwood particles having a moisture content of 6%.

Example 1

(CONTROL)

Lignocellulose Material without any binder was formed into a mat measuring 61 cm×122 cm×20 cm. This mat was then placed between two sheets of Typar landscape spunbound polypropylene fabric and placed in a Newman Hydra Press Model HP-138. A transmitter probe corresponding to transmitter probe 1 shown in FIGS. 1 and 2 was inserted midway between the top and bottom of Lignocellulose Material at a distance of 20 cm from the horizontal center and to the right of the horizontal center of Lignocellulose Material, and to a depth of 20 cm in the manner illustrated in FIG. 1.

A receiver probe corresponding to receiver probe 4 shown in FIGS. 1 and 2 was inserted midway between the top and bottom of Lignocellulose Material at a distance of 6 cm from the horizontal center and to the left of the horizontal center of Lignocellulose Material and to a depth of 20 cm.

The transmitter and receiver probes were separated by a gap of 12 cm and were parallel.

The transmitter probe was connected to the transmitter transducer output of the NDT-910 Ultrasonic Tester. The receiver probe was connected to the receiver transducer input of the NDT-910 Ultrasonic Tester and amplified to a ±1 volt peak to peak level. The NDT-910 Ultrasonic Tester is available from NDT International, Inc., West Chester, Pa. The NDT-910 Ultrasonic Tester was programmed to emit a one-half cycle pulse of 60 KHz at a repetition rate of 100 pulses per second to drive the transmitter probe. The amplified receiver signal was sent to an analog digital converter board Model CD255 which is commercially available from GAGE Applied Sciences, Inc., Montreal, Canada and mounted in an IBM PC compatible computer with a 100 MHz Intel Pentium processor. The converter board was programmed to sample the incoming pulse at a rate of one million samples per second. The beginning of the transmitted pulse triggered data collection of the received pulse and 1024 data points were saved to represent the pulse.

To improve the signal to noise level, the computer was programmed to collect and time average 100 ultrasonic pulses. The averaged ultrasonic pulse was displayed on a computer monitor as a time dependent signal. (See FIG. 3.)

Figure 4:
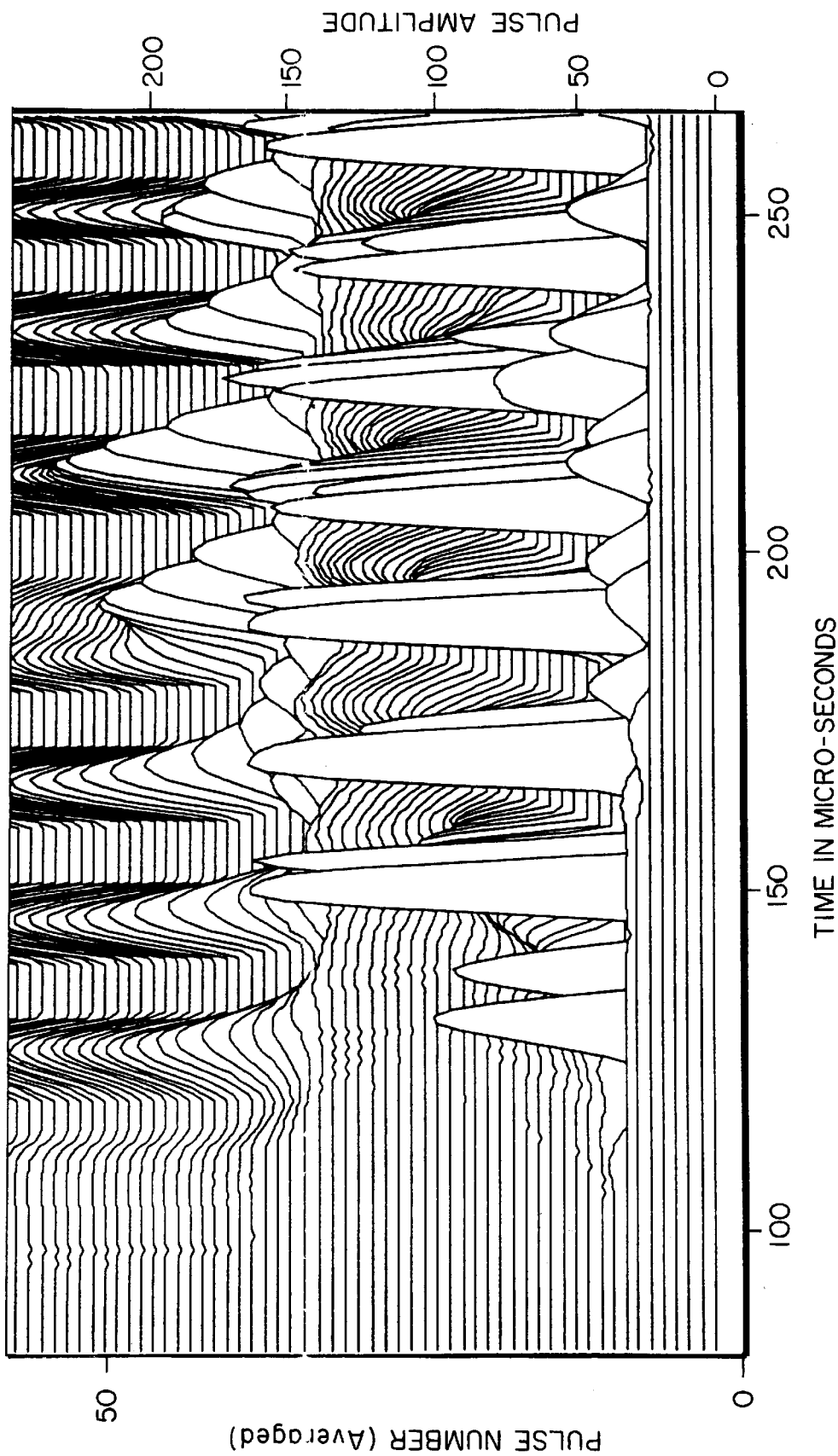
FIG. 4 is a three-dimensional hidden line histogram of the ultrasonic pulses collected in Example 1.

FIG. 4 is a three dimensional, hidden line histogram of the ultrasonic pulses collected during the press run using 0% binder. The X axis is the time in microseconds into the pulse data collection window, or time into the ultrasonic pulse. The Y axis is the amplitude of the ultrasonic pulse. The Z axis is the time averaged pulse number, or time into the press run.

Example 2

Example 1 was repeated with the exception that the Lignocellulosic Material was mixed with Binder Material in an amount such that the final mixture contained 5% by weight Binder Material.

Figure 3:
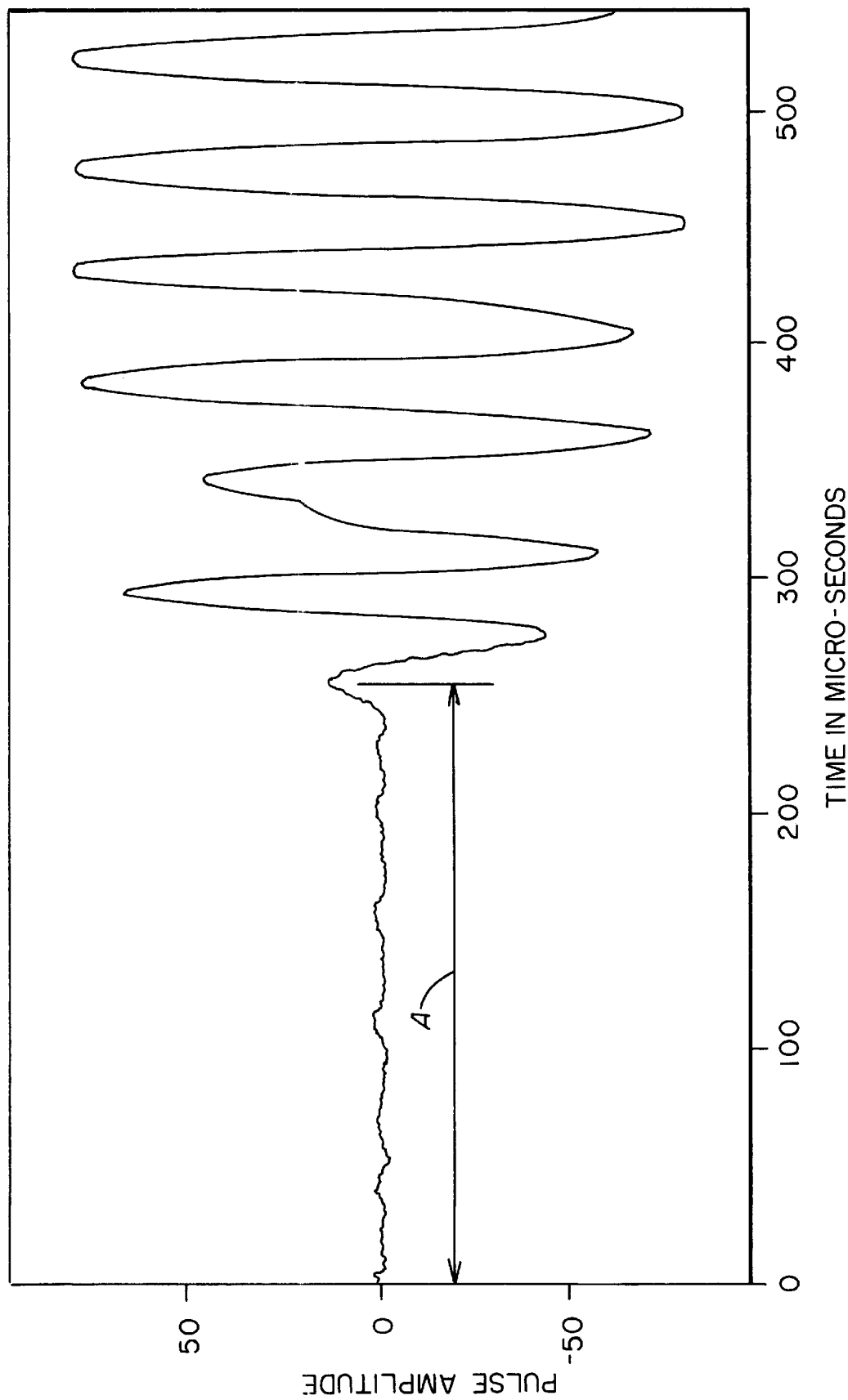
FIG. 3 is a graphic illustration of the averaged ultrasonic pulse as a time dependent signal for the composite material produced in Example 1.

Because the distance between the transmitter and receiver probes was held constant, the velocity of the acoustic waves and Young's modulus (or the state of cure) was inversely proportional to the transit time between the beginning of the received pulse data collection and the first half cycle of the received pulse, represented as interval A in FIG. 3.

It was not necessary to calculate the velocity or Young's modulus directly. The trend in Transit Time represented by interval A in FIG. 3 indicates the state of the cure of the binder. As Young's modulus increases, the interval A in FIG. 3 will shorten and the first half cycle of the ultrasonic pulse will move to the left. If Young's modulus decreases, interval A will lengthen and the pulse will move to the right.

Figure 5:
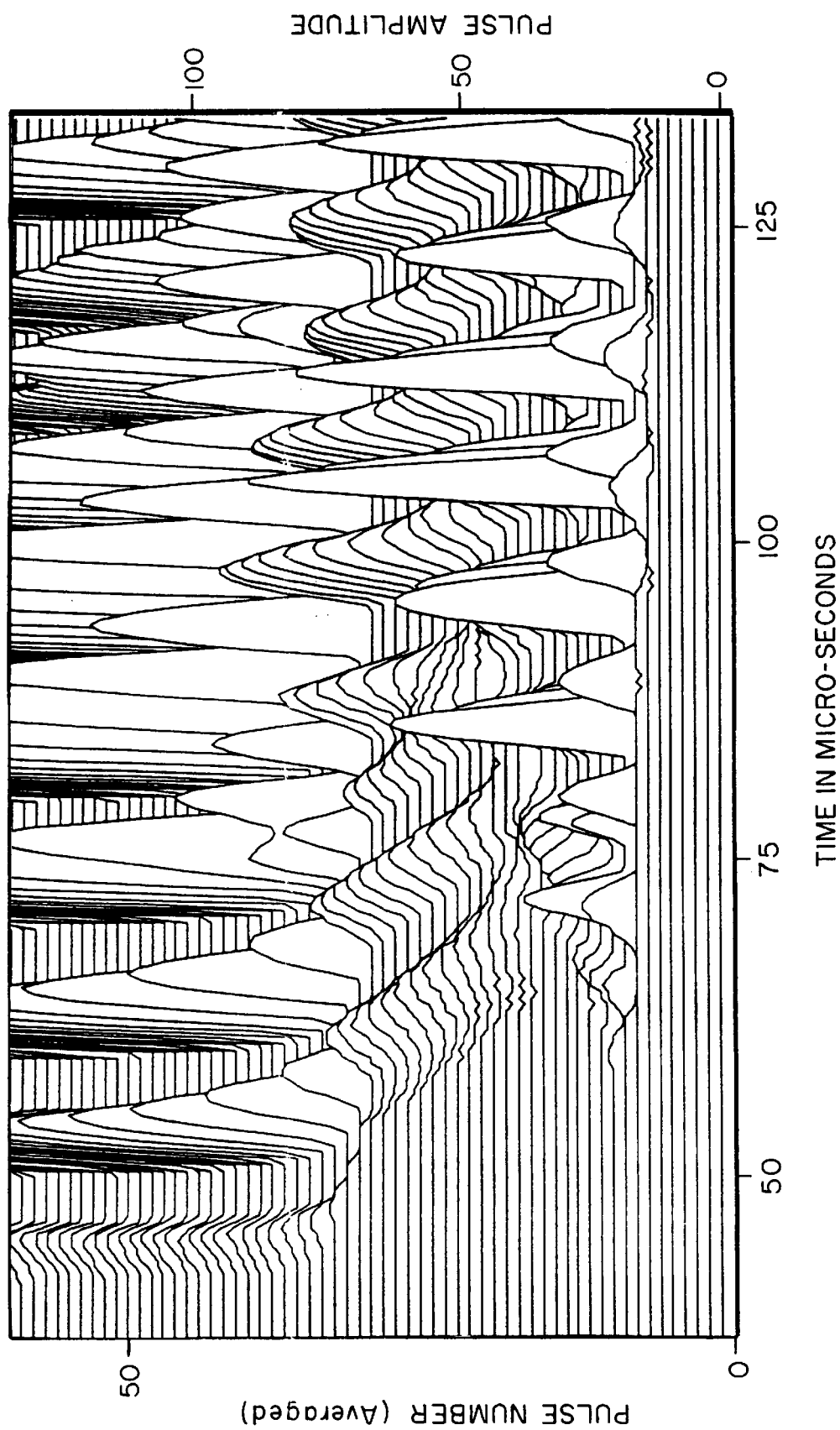
FIG. 5 is a three-dimensional hidden line histogram of the ultrasonic pulses collected in Example 2.

FIG. 5 is a three dimensional, hidden line histogram of the ultrasonic pulses collected during a press run using any composite-forming mixture with 5% by weight Binder Material. The X axis is the time in microseconds into the pulse data collection window, or time into the ultrasonic pulse. The Y axis is the amplitude of the ultrasonic pulse. The Z axis is the time averaged pulse number, or time into press run. The position of the first half cycle of the ultrasonic pulse moves to the left as the press closes and the wood mat density increases. The steam is then turned on and the pulse moves to the right as the wood is plasticized. During the plasticization process, the received ultrasonic pulse may become undetectable due to the poor sound transmission quality of the plasticized wood and the acoustic noise of the steam injection. Shortly after the steam is turned on, the binder starts to cure, and the pulse reappears. Young's modulus will increase with the pulse moving to the left. As the binder fully cures, the interval A in FIG. 3 will reach a minimum with the pulse reaching its leftmost position.

Figure 6:
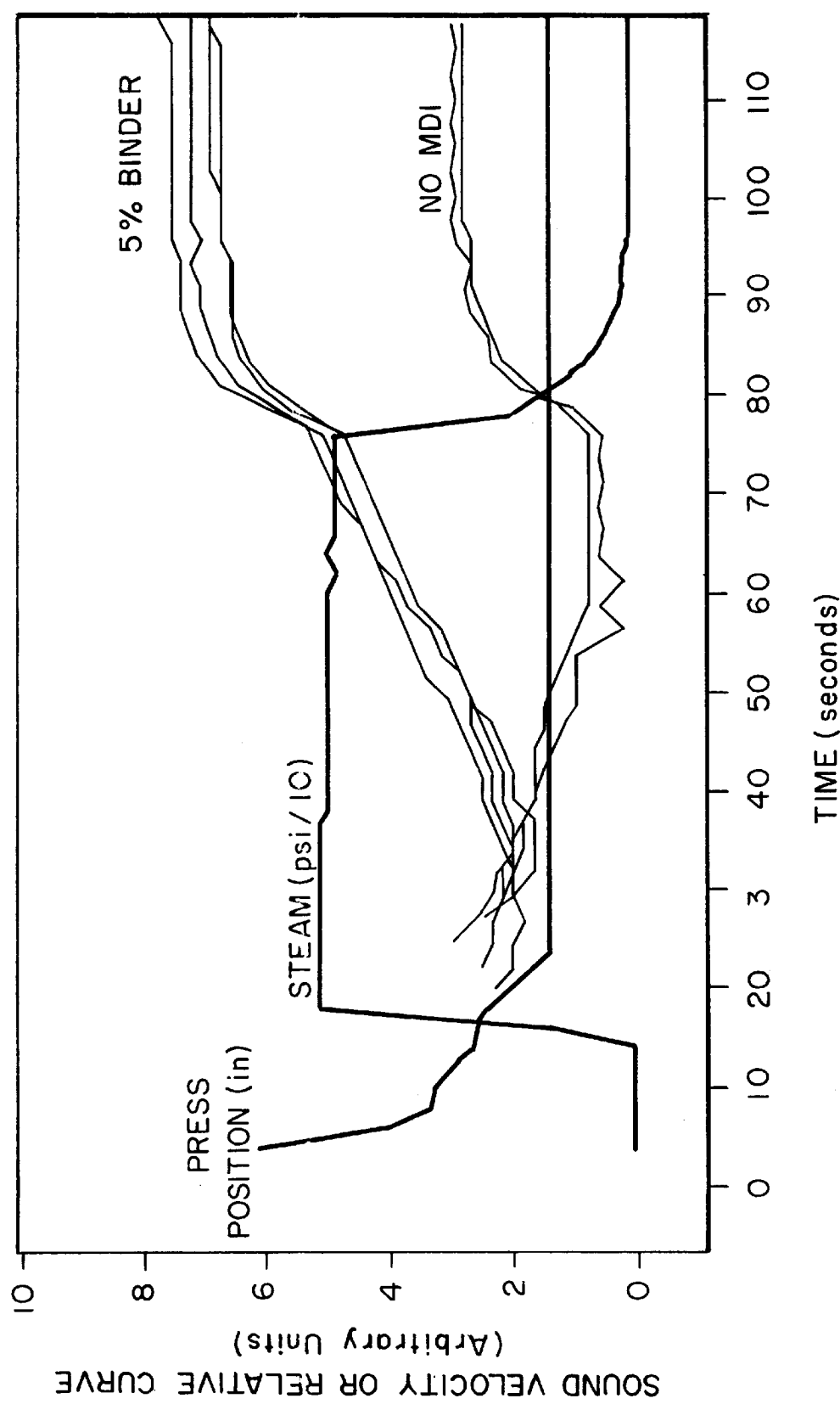
FIG. 6 is a graphic representation of the relative cure trends for 4 press runs conducted in accordance with Example 2 and 2 press runs in accordance with Example 1.

FIG. 6 illustrates the relative cure trends as the inverse transit times or 4 press runs with 5% Binder Composition and 2 runs with 0% Binder Composition. The Y axis is in arbitrary units for relative cure. Overlaid on the cure trends is the trend of the distance between the two press platens showing the press closing to 1.5 inches with the Y-axis in inches. Also overlaid on the cure trends is the steam injection pressure divided by 10 during the press cycle. The steam is turned on at 15 seconds into the press run to a pressure of 50 psi and turned off at 75 seconds into the press run. The cure trends take a jump when the steam pressure is turned off at 75 seconds into the press run due to the change in pressure. This jump can be corrected for by subtracting the 0% binder trend. From the cure trends, it is obvious that the binder is fully cured at 95 seconds into the press run. The press can then be opened and the board removed. It was not necessary to monitor the press on a continuous basis. Once the press run had been characterized for a given set of process parameters using the ultrasonic cure monitor and the cure time had been determined, the cure time would not change unless the process parameters were changed. This eliminates the need to permanently mount the ultrasonic transducers on the walls of the press platens.

Although the invention has been described in detail in the foregoing for the purpose of illustration, it is to be understood that such detail is solely for that purpose and that variations can be made therein without departing from the spirit and scope of the invention except as it may be limited by the claims.

What is claimed is:

1. An improved process for the production of a composite lignocellulose article in a press having a top plate and a bottom plate comprising
   a) inserting a transmitter probe capable of emitting an ultrasonic wave into the material from which the composite article is to be made,
   b) inserting a receiver probe capable of receiving an ultrasonic wave emitted by the transmitter probe into the material from which the composite article is to be made at a position sufficiently distant from the transmitter probe to allow measurement of ultrasonic acoustic wave velocity through the material from which the composite is to be made,
   c) causing the transmitter probe to send an ultrasonic signal of predetermined frequency through the material from which the composite article is to be made to the receiver probe,
   d) measuring the pulse velocity of each wave of the ultrasonic signal as it passes through the material from which the composite article is being produced,
   e) comparing the measured pulse velocity of the waves of the ultrasonic signal to the pulse velocity of waves of an ultrasonic signal at same frequency as those waves were passed through a completely cured composite article made from the same material, and
   f) removing the composite article from the press when the ultrasonic wave pulse velocity measured equals the ultrasonic wave pulse velocity of a completely cured composite article.

2. The process of claim 1 in which the material from which the composite is being made is wood fiber strands coated with an isocyanate-based binder composition.

3. The process of claim 2 in which diphenyl methane diisocyanate is the isocyanate upon which the binder composition is based.

4. The process of claim 1 in which the ultrasonic wave sent through the material from which the composite is being made has a frequency of from 40 to 60 KHz.

5. An apparatus useful for monitoring the cure time of a binder during the production of a lignocellulosic composite material comprising:
   a) a transmitter probe capable of transmitting ultrasonic, acoustic waves through composite-forming material when inserted into that composite forming material,
   b) a receiver probe capable of receiving ultrasonic, acoustic waves passing through the wood composite-forming material when inserted in that composite-forming material at a suitable distance from transmitter probe a),
   c) means for measuring pulse velocity of the ultrasonic waves passing through the composite-forming material, and
   d) means for comparing the pulse velocity measured by measurement means c) with the pulse velocity of waves passing through a composite-forming material processed under the same conditions in which the binder was completely cured.

6. The apparatus of claim 5 in which the transmitter probe and the receiver probe are the same in structure.

7. The apparatus of claim 6 in which the transmitter probe and the receiver probe are composed of
   (1) an ultrasonic transducer,
   (2) a metal disc attached to transducer (1) which is adapted to receive a wave guide, and
   (3) a wave-guide which is attached to metal disc (2).

* * * * *